United States Patent [19]

Anderson et al.

[11] 4,453,551

[45] Jun. 12, 1984

[54] APPARATUS FOR PATTERN RECOGNITION OF ECG SIGNALS FOR DETECTING FIBRILLATION

[76] Inventors: John Anderson, 16 Tor Grange, Carlston Ave., Holywood, Co.Down; David Weir, 2, Lynda Ave., Jordenstown, Newtown Abbey, both of Ireland

[21] Appl. No.: 237,984

[22] Filed: Feb. 25, 1981

[51] Int. Cl.³ ................................................ A61B 5/04
[52] U.S. Cl. ...................................................... 128/704
[58] Field of Search ................................. 128/702–705

[56] References Cited

U.S. PATENT DOCUMENTS

| | | | |
|---|---|---|---|
| 3,144,019 | 8/1964 | Haber | 128/702 |
| 3,524,442 | 4/1970 | Horth | 128/703 |
| 3,698,386 | 10/1972 | Fried | 128/705 |
| 3,707,959 | 1/1973 | Wilton-Davies | 128/703 |
| 3,889,659 | 6/1975 | Lutes | 128/703 |
| 3,940,692 | 2/1976 | Neilson | 128/702 |
| 4,124,894 | 11/1978 | Vick et al. | 128/703 |

*Primary Examiner*—William E. Kamm
*Attorney, Agent, or Firm*—Karl W. Flocks; Sheridan Neimark

[57] ABSTRACT

Physiological electrical signals such as electrocardiograph signals ae converted to digital form, amplified to a standard maximum amplitude and analyzed by a computer. The analysis may calculate the ratios of energies above and below an isoelectric line, the statistical distribution of gradients, the frequency of a maximum negative gradient and the zero content of the signal. The analysis may be used for detecting ventricular fibrillation.

15 Claims, 17 Drawing Figures

FLOW DIAGRAM OF COMPLETE SYSTEM WITH NEW ENERGY ROUTINE.

LOW PASS FILTER
$R_1 = R_2 = 39\ K\Omega$
$C_1 = C_2 = 0.22\ \mu F$
$f_0 \simeq 18.5\ Hz$ HIGH PASS FILTER
$R_3 = 560\ K\Omega$
$R_4 = 120\ K\Omega$
$C_3 = C_4 = 0.22\ \mu F$
$f_0 \simeq 3\ Hz$

FLOW DIAGRAM OF COMPLETE SYSTEM WITH NEW ENERGY ROUTINE.

FIG. 11

ENERGY RATIO CALCULATED OVER A PERIOD OF 500 SAMPLES (2 SEC).

ENERGY FLOW CHART

FIG. 12

Flow chart of zero content and variance of slope calculation.

APPARATUS FOR PATTERN RECOGNITION OF ECG SIGNALS FOR DETECTING FIBRILLATION

DESCRIPTION OF THE INVENTION

This invention relates to methods and apparatus for pattern recognition of electrical signals of physiological origin. The invention may be used for automatic diagnosis of heart conditions, especially for detection of conditions which may require defibrillation.

Ventricular fibrillation often occurs during a heart attack and is commonly fatal unless treatment is applied rapidly. Ventricular fibrillation is a condition in which the heart has ceased to pump or has spasmodically irregular contractions, accompanied by chaotic electrical activity.

The operation of a patient's heart may be monitored using an electrocardiograph, which receives electrical signals from the heart through a pair of electrodes, commonly attached to the patient's chest, and displays the electric pulses received on a display screen, usually a cathode ray tube, using a suitable time-base. The trace obtained can be inspected by a physician and indicates the behaviour of the heart. However correct interpretation of an electrocardiograph (ECG) trace requires considerable training because of the variety of heart conditions giving rise to different traces, some of which are superficially similar. An incorrect diagnosis from an ECG trace could have very grave consequences.

It is desirable to process the signals from an ECG automatically to distinguish the normal electrical behaviour of the heart (normal sinus rhythm) from abnormal behaviour, especially to identify fibrillation which will generally require very rapid treatment. Such processing might be carried out using a series of electronic circuits which together form a pattern recognition system. However such an arrangement has the disadvantage that the characteristics of the signal received from the patient, as evident from the shape of the ECG trace when displayed on a screen, are liable to be distorted by the electronic circuits, including RC circuits, used so that a false diagnosis of certain heart conditions may be obtained. This difficulty is exacerbated by the fact that no single measured criterion can be used to distinguish reliably ventricular fibrillation from other heart conditions and so several parameters must be analyzed. This makes the circuitry required complicated, bulky and expensive and increases the probability of distortion.

The present invention is intended to provide a method and apparatus for analyzing electric signals in which distortion of the signal by the apparatus itself is reduced to a minimum.

It is applicable to automatic analysis of physiological electrical activity, especially the electrical behaviour of the heart, particularly to distinguish ventricular fibrillation from normal sinus rhythm and from other conditions such as ventricular tachycardia.

According to one aspect of the invention there is provided pattern recognition apparatus comprising a pair of electrodes adapted to be connected to the body of a patient to receive an electric signal fluctuating about an isoelectric line, means for sampling the signal received at intervals and converting the magnitudes of the samples from analogue to digital form, automatic gain control means for standardising the magnitudes of the digitised samples to a predetermined maximum value, and a computer arranged to analyze the standardised samples to detect an abnormal physiological condition.

Embodiments of the invention will be described below as applied to an electrocardiograph, although it will be understood that the invention in its broadest aspect may be applied to the pattern recognition of electric signals from other sources.

A preferred embodiment of the invention has been chosen for purposes of illustration and description and is shown in the accompanying drawings forming a part of the specification, wherein:

FIGS. 1 to 7d are schematic views of various ECG trace signals.

In one embodiment the apparatus of the present invention, when applied as an electrocardiograph comprises a pair of electrodes which may be attached to the patient's body in order to detect the electrical activity associated with the heart beat. The electrodes may be implanted but it is generally more desirable to use external electrodes which are attached to the chest. The electrodes are connected by suitable leads to the remainder of the apparatus which processes the signals received.

The signals received through the electrodes are fed to an analogue→digital converter in which they are expressed in digital form and the digitised signals are then analyzed. Once expressed in digital form, the information obtained from the ECG will not be altered by subsequent circuitry. The analogue-digital converter samples the signal received from the electrodes at suitable intervals, for example 0.004 seconds and the information thus derived may be stored in a digital memory.

When analyzing an ECG signal it is desirable to study the QRS complex of the signal obtained, which is the component characteristic of normal sinus rhythm. However the QRS complex is generally accompanied by other signal components which may be considerable amplitude, such as P and T components. In order to eliminate these components it is possible to attenuate all frequencies from the original signal below 3 HZ and above about 18 HZ, the frequency range in which the QRS complex is situated. This may be achieved by inserting low- and high-pass filters in the circuit between the electrodes and the analogue-digital converter. A suitable filter arrangement is a Sallen and Key band pass filter. The RC elements in such a filter will introduce a small distortion in the wave-form received by the converter, but it has been found that this distortion is small enough not to interfere seriously with subsequent analysis of the signal.

Figures 1, 2, 3A:
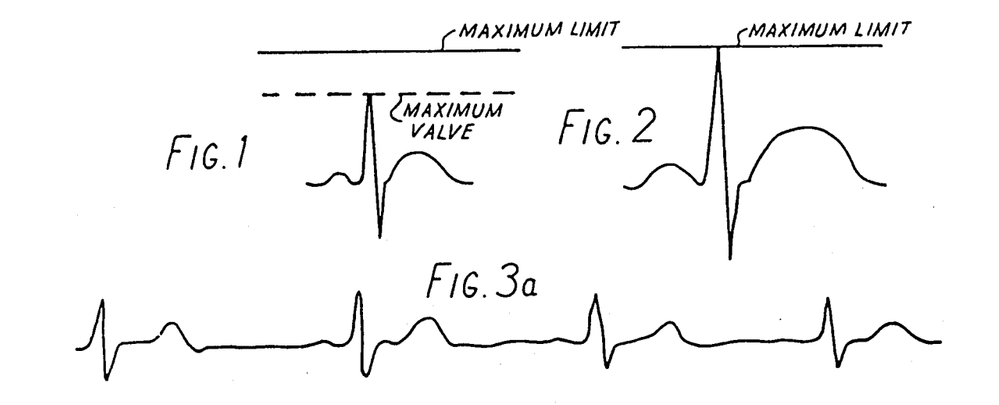

When the real-time digitised signals have been stored they are first subjected to an Automatic Gain Control (AGC) sub-routine to standardise their amplitude: this step is required because the amplitude of an ECG signal may vary considerably from patient to patient. The AGC sub-routine takes the greatest value from a suitable number of successive sample values (such as 250) and deduces from the value a scale factor by which all the samples are then multiplied. The scale factor is chosen such that the highest value, after multiplication, corresponds to a maximum limit which is determined by the operator. Reference is made to FIG. 1, in which the trace shown is that of an unmultiplied ECG trace and the maximum limit set by the operator is shown: FIG. 2 shows the appearance of the trace after multiplication of all the samples by the scale factor. Thus:

Value of a sample after $AGC =$ $$\frac{\text{Value before } AGC \times \text{Maximum limit}}{\text{Maximum value}}$$

This procedure is repeated for successive batches of samples until a suitable total number of successive samples (such as 1000 samples) have been processed. The multiplied samples are then stored in a memory.

After the AGC stage the multiplied samples may then be subjected to a series of tests to detect an abnormal physiological condition. These tests may be carried out using a computer installation containing a programme comprising a series of sub-routines to carry out the various tests. The following description describes a series of tests which may be used to detect ventricular fibrillation.

One such test depends on the presence of a substantial amount of zero content (isoelectric segments) in the normal sinus rhythm wave-form, whereas the zero content in ventricular fibrillation is very small. This is evident from FIG. 3a, which is an ECG trace of normal sinus rhythm, and from FIG. 4a which is an ECG trace from ventricular fibrillation. If the computer carries out a sub-routine to measure the proportion of the samples having a zero value, a proportion above a predetermined amount may be considered as "normal" whereas a proportion below this amount is taken as indicating possible fibrillation.

Figures 3B, 4A:
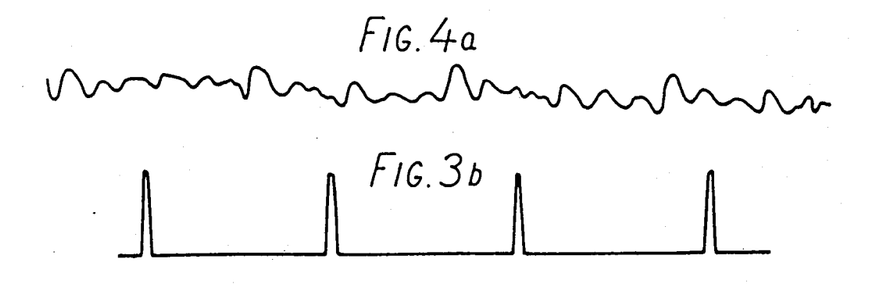
Figure 4B:
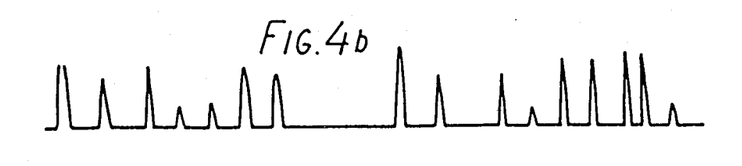

As may be seen from FIG. 3a the base-line of a normal sinus rhythm signal is not perfectly isoelectric owing to noise and the presence of P and T waves, which may have passed the pass-band filter in an attenuated state. This base-line irregularity may be avoided by using a floating zero which may be set by the operator at a suitable value, e.g. 20% of the maximum limit above the true base-line. FIGS. 3b and 4b, show the effect of this operation on the traces of FIGS. 3a and 4a respectively. It can be seen that the zero content of the normal sinus rhythm (NSR) trace is increased by a large amount and that of ventricular fibrillation (VF) while being increased somewhat, is still much less than that of NSR.

Using this test, a proportion of zero content of at least 680 samples from every 1000 (68%) is regarded as normal.

Figure 5:
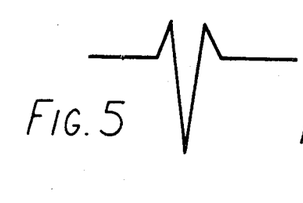

The validity of this test may be affected by distortion introduced by the band-pass filter. Some types of ECG trace may be distorted to produce trace elements of shape shown in FIG. 5 and the presence of these elements will reduce the zero content of the trace. In order to eliminate this effect it is possible to invert the signal and repeat the above-mentioned test, still using the floating zero. In most cases inversion of the signal gives an increased zero content and the signal is again classed as normal.

Distortion of the original signal caused by the filter can be removed by omitting the filter and introducing a further sub-routine into the programme to remove the undesired frequencies. However use of such a sub-routine makes the programme much more complex and consumes computer time which is valuable in an "on-line" system of this nature.

Figure 6:
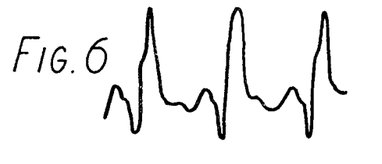
Figure 7A:
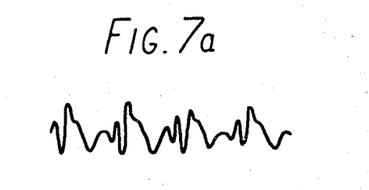
Figure 7B:
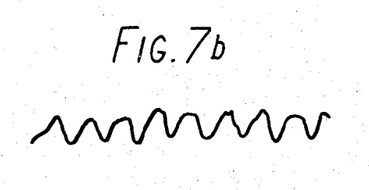
Figure 7C:
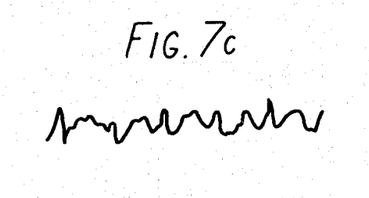
Figure 7D:
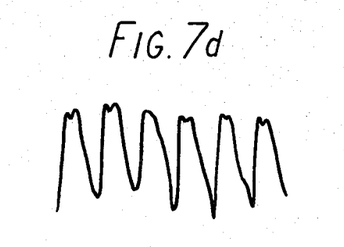

The above-described test can be ambiguous on its own because of other possible heart conditions, such as ventricular tachycardia, which also have a low zero content but are distinct from fibrillation. A portion of an ECG trace showing ventricular tachycardia is shown in FIG. 6. Ventricular tachycardia has a high beat rate but is distinguished from fibrillation in that it is essentially regular, so that the ratio of the energies contained in the ECG trace above and below the isoelectric line is essentially constant. Thus, if the energies above and below the isoelectric line for a suitable number of successive samples are measured, and the ratio of these energies calculated, and this calculation repeated for successive groups of samples, the energy ratios of the successive groups or "windows" may be compared. If these ratios are substantially the same, then fibrillation may be eliminated as a possible condition.

It has been found that the energy ratio prepared as above is appreciably affected by the presence of base-line noise, which is random and cannot be controlled. The effect of base-line noise can be eliminated by setting amplitude limits above and below the base-line and eliminate the signals between these limits from the energy totals above and below the isoelectric point. These limits are chosen experimentally. Elimination of the effect of noise in this way reduces the variability of the energy ratios obtained from normal sinus rhythm.

A suitable duration for each "window" is 2 seconds, corresponding to 500 successive ECG readings at 0.004 second intervals. It has been found that durations much shorter than this (e.g. 1 second) do not allow analysis of very low heart beat rates. Periods of 3 seconds or above tend to even out the energy ratio even in the event of irregular heart activity so that a "normal" result may be obtained when fibrillation is actually occurring.

Using 2-second "windows" and elimination of noise as mentioned above a result from this test is considered "normal" if the energy ratio is within 20% of the mean ratio for at least 7 out of 10 windows.

An alternative way of carrying out this test is to measure the energy ratios of successive windows as described above and calculate the variance. However this procedure is less reliable as a ratio from a single window which differs widely from the others has a very big effect on the variance.

A third test for distinguishing normal sinus rhythm from ventricular fibrillation comprises analyzing statistically the slopes of the ECG signal. It will be seen from FIGS. 3a and 4a that the NSR trace has a high proportion of zero gradient and that most of the non-zero gradients are relatively steep. On the other hand the VF trace has little zero gradient and a more or less random distribution of non-zero gradient. If the traces are differentiated and a histogram is plotted showing the statistical distribution of the slopes of each trace, the histogram for SNR shows a much narrower distribution of slopes than VF.

The width of these histograms may be expressed algebraically as the variance (the square of the standard deviation) of the population of the gradients of the traces. The variance of a trace may be calculated using a programme sub-routine by differentiating the ECG trace by suitable processing of the samples stored in the computer and slotting the gradients obtained in a series of "pigeon-holes" (e.g. +20, +10, +5, 0, −5, −10, −20). The variance $\sigma^2$ is then calculated by the sub-routine from the following equations:

$$\bar{x} = \frac{1}{N} [f_1 x_1 + f_2 x_2 \ldots f_n x_n]$$

$$\sigma^2 = \frac{1}{N} [f_1(x_1 - \bar{x})^2 + f_2(x_2 - \bar{x})^2 \ldots f_n(x_n - \bar{x})^2]$$

where
$\bar{x}$ = mean value of the gradients obtained
N = number of gradients obtained,
xn = value of a gradient,
fn = frequency of xn,
n = number of pigeon-holes.

It is considered that a variance of below 75 is representative of SNR and a variance above this figure indicates ventricular fibrillation.

The above-mentioned tests together give a reliable detection of ventricular fibrillation but there are certain types of tachycardia for which they can give a false indication of fibrillation as the zero content and variance values may be outside the above-mentioned limits. Some types of tachycardia which may result in such a false detection are shown as ECG traces in FIGS. 7a-d and they can fulfil at least two of the above-mentioned criteria to indicate fibrillation.

However it will be noted that all the traces 7a-d contain at least a weak or distorted QRS complex occurring at regular intervals and this complex is associated with the steepest negative slope of the whole cycle of operation of the heart. If this slope is detected and the interval between successive detections (the R—R interval) measured, comparison of the intervals will indicate the presence or absence of a regular QRS complex.

This comparison can be carried out by differentiating a suitable number of successive samples (such as 250) and taking the steepest negative slope as a reference value. The remainder of the stored samples are then differentiated and scanned and the time intervals at which like slopes occur are recorded. A "like" slope is one which is with a predetermined range on either side of the reference value: a suitable range is 20%.

This scanning is continued until a suitable number of like slopes (such as 8) have been detected. The R—R intervals between them are then compared and if a predetermined proportion (such as 5 out of 8) are equal within predetermined limits absence of fibrillation is recorded. If this criterion is not met, "rate irregular" is indicated and if no detections at all are made in a given period, such as 3 seconds, "no rate detected" is indicated.

This test may give a false result if any artifact occurs during the "learning" period in which the reference value is established. Any artifact is likely to produce a negative slope which is greater than that of the QRS complex and consequently becomes selected as the reference value. This possibility may be eliminated by following the procedure for establishing a reference value twice over adjacent 250-sample batches and taking the lower of the two values thus established as the reference value.

Figure 8:
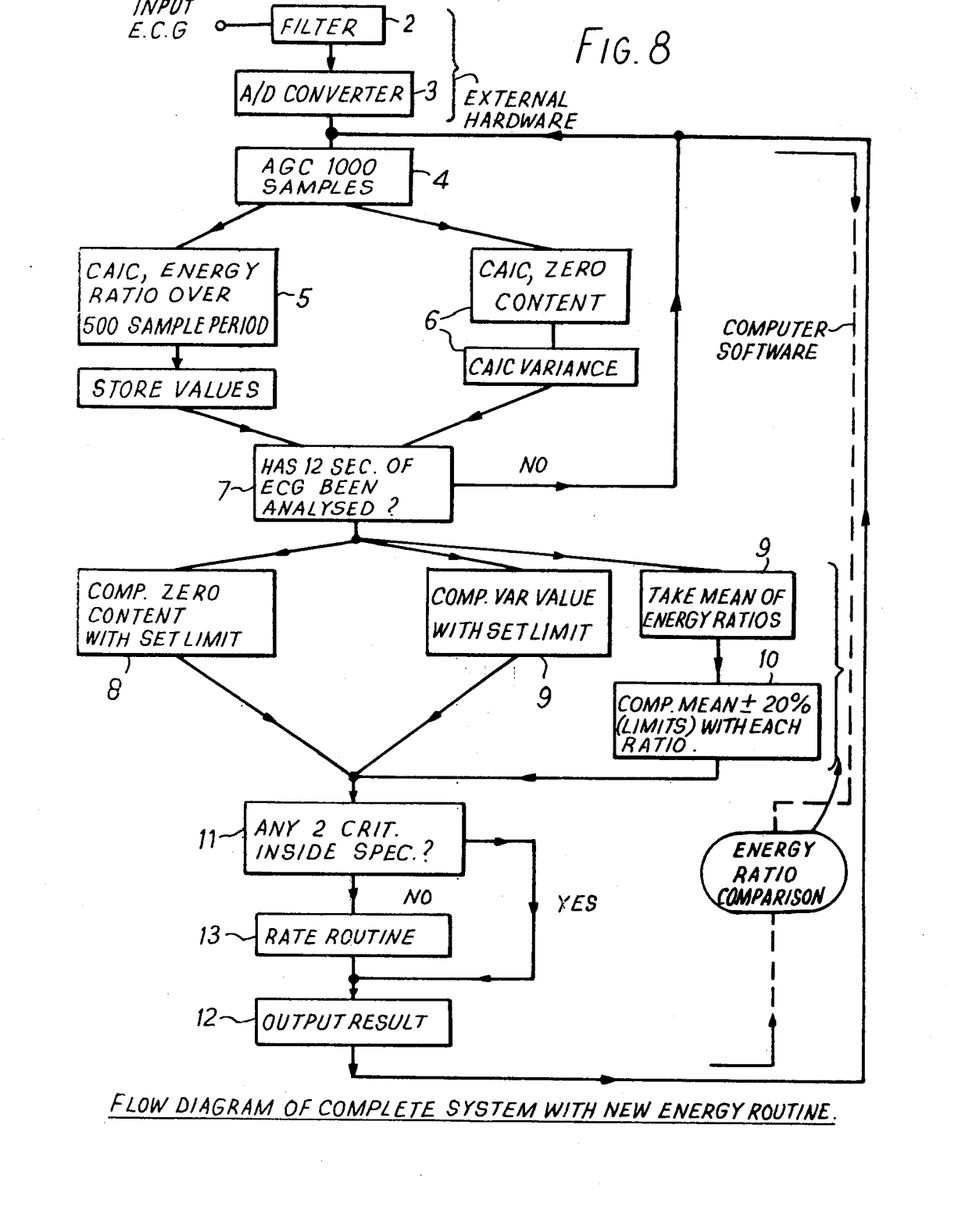
FIG. 8 is a schematic flow diagram of a pattern recognition system in accordance with the present invention.

In the accompanying drawings, FIG. 8 shows schematically a flow diagram of a pattern recognition system intended to carry out the above-mentioned functions.

Figure 9:
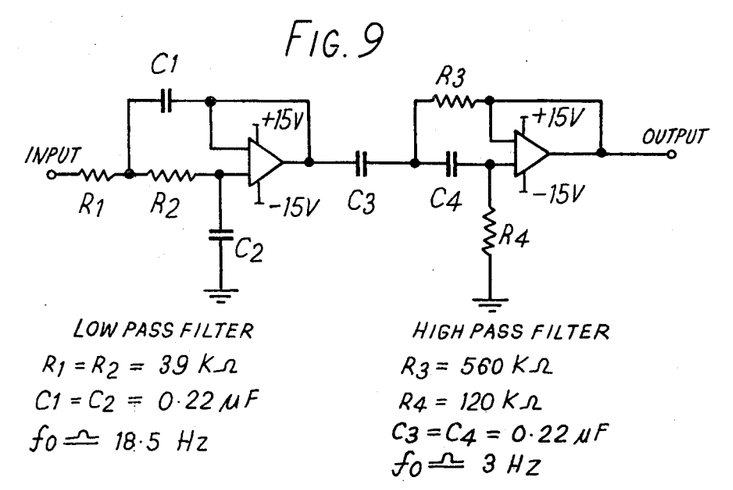
FIG. 9 is a schematic diagram of a band-pass filter circuit used with the present invention.
Figure 10:
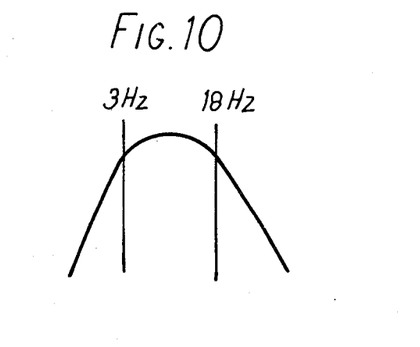
FIG. 10 is a schematic diagram showing the frequency response of said band-pass filter.

Referring to the diagram, a conventional ECG unit comprising electrodes to receive electric signals from a patient feeds the signals directly to a filter unit 2. Unit 2 comprises a Sallen and Key band-pass filter, the circuit of which is shown in FIG. 9 together with the values of the circuit components. The frequency response of this filter is approximately as shown in FIG. 10.

The filtered signal is then passed to an analogue→digital converter of conventional type 3 in which the signal is sampled at intervals of 0.004 seconds and the samples are expressed in digital form. The digitised signals are then passed to a computer installation for subsequent processing.

In one suitable arrangement the analogue→digital converter is an 8-bit converter interfaced with a CA1 naked mini ALPHA 16 mini-computer and all processing of the samples from the converter is carried out numerically by sub-routines of the computer programme.

The digitised signals are first multiplied in the automatic gain control stage 4 by a scale factor related to the maximum value observed in 250 successive signals to give standardised values as explained above: the maximum limit value may be determined by an operator. The standardised samples are stored in a memory and when the memory contains 1000 successive samples the samples are subjected to a series of tests as described below.

Figure 11:
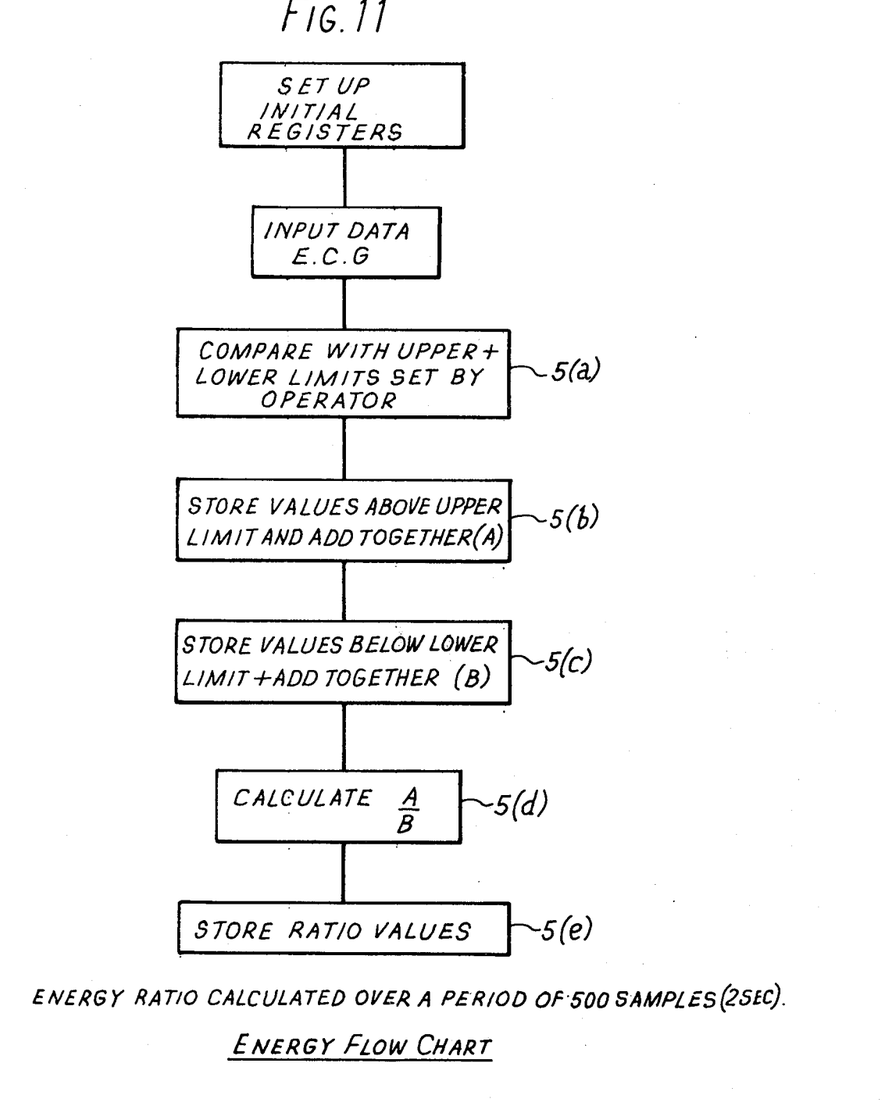
FIG. 11 is a flow chart showing the energy ratio calculation steps of the present invention.

The samples from stage 4 are fed to an energy ratio calculation stage 5 in which an energy ratio for batches of 500 samples, representing periods of 2 seconds, are calculated as described above. The steps in this operation are shown in the flow chart 11. After setting up the initial registers the batches of samples are fed into them and compared with positive and negative values, pre-set by the operator, corresponding to amplitude limits above and below the isoelectric line (stage 5a). The samples above this positive value are stored and added together for the batch of 500 successive samples (stage 5b) and the samples below the negative value are likewise stored and added together (stage 5c). The total obtained from stage 5b is then divided from that from stage 5c (stage 5d) and the ratio is itself stored (5e). This process is repeated for successive batches of samples, to give a series of energy ratios, until the samples from 12 successive seconds of ECG signal have been processed (stage 7). A set of 6 energy ratios, derived from 6 successive batches of 500 samples each, is thus obtained.

Figure 12:
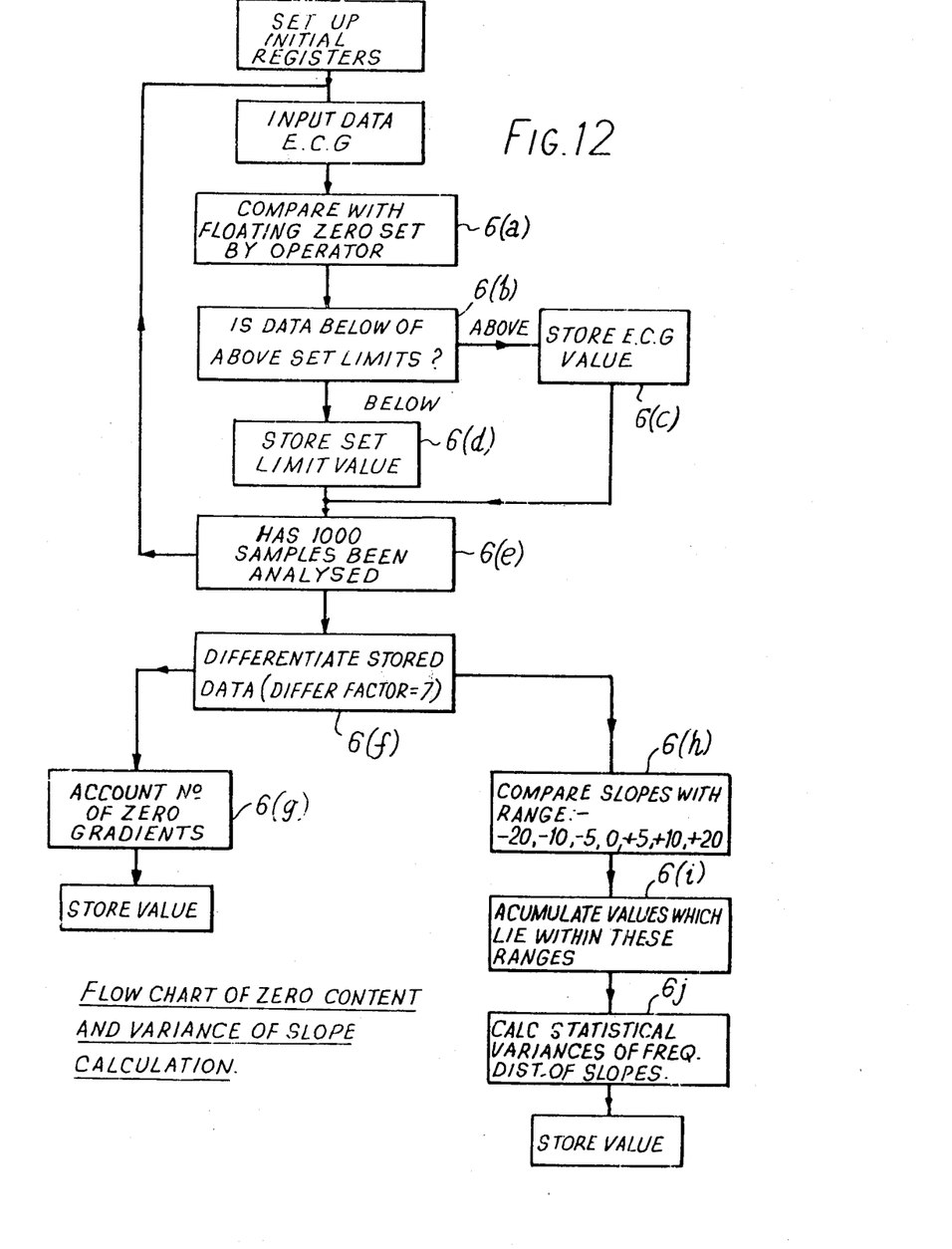
FIG. 12 is a flow chart showing the zero content and slope variance steps of the present invention.

The samples from the automatic gain control stage 4 are also passed to a zero content and slope variance stage 6, which is shown in greater detail in flow diagram 12. After setting up the initial registers required the samples from stage 4 are fed into them. The samples are then compared with a floating zero set by the operator, for example at a value of 20% above the base-line of the maximum limit (stage 6a). Stage 6b determines whether each sample is above or below the floating zero: if a sample is above the floating zero the sample is stored as such and if it is below it is the floating zero value which is stored (stages 6c and 6d). Stage 6e causes this procedure to be continued until a batch of 1000 samples have been processed and stored in this manner.

The successive samples of the batch are then differentiated with respect to time, using a differentiation factor of 7 (stage 6f) to produce a series of gradients from successive groups of stored samples. The gradients obtained from groups of samples from stage 6d, which in fact are samples from the floating zero, are zero: the ECG samples from stage 6c give non-zero gradients. All these gradients are processed at stage 6g in which the proportion of zero gradients in the total number of gradients obtained is calculated. The proportion of zero gradients is then stored.

The gradients obtained are also processed at stage 6h in which the gradients are allocated or "slotted" into a series of pigeon holes having values, 20, 10, 5, 0, −5, −10 and −20. The number of gradients in each slot is then totalled (stage 6i) and the statistical variance of the frequency distribution thus obtained is calculated (stage 6j). The variance value obtained for the batch of 1000 samples is then stored.

When 12 seconds of ECG signal have been analyzed as above the stored magnitudes obtained are compared with predetermined criteria. The proportion of zero gradients obtained from stage 6g is compared with a set limit which is set at 68% (stage 8) and if it exceeds this value the ECG signal is classed as normal using this criterion: if it is less, an "abnormal" signal is generated. The variance value from stage 6j is compared with the set limit of 75 (stage 9) and if it is less than this value the ECG signal is classed as normal using this criterion: if it is greater an "abnormal" signal is generated.

The mean of the energy ratios from stage 5d is calculated (stage 9) and the number of ratios which is within 20% of this mean is calculated (stage 10). The ECG signal is classed as normal by this criterion if at least 4 out of 6 of the energy ratios are within these limits: if 3 or less are outside these limits an "abnormal" signal is generated.

Figure 13:
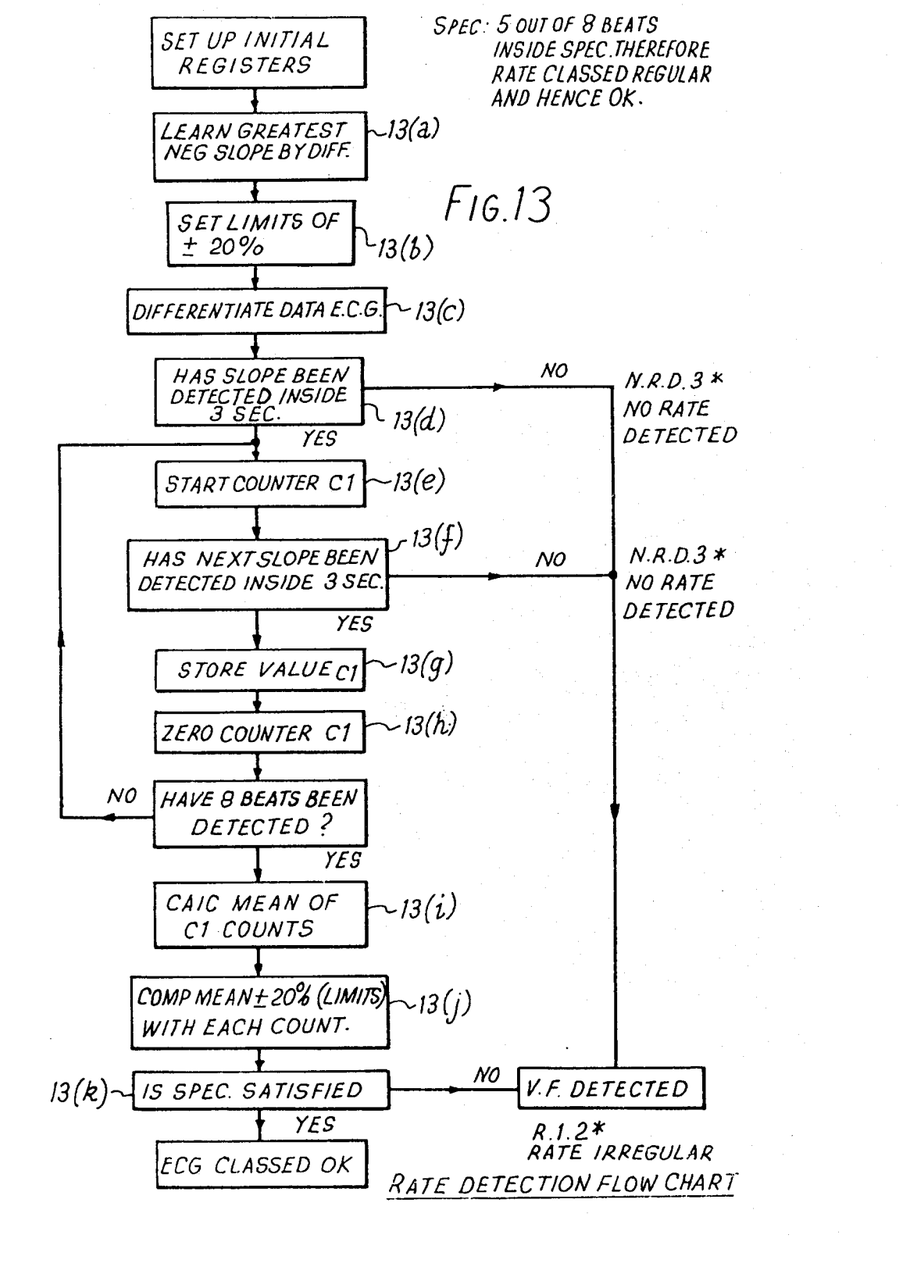
FIG. 13 is a flow chart showing the rate detection routine used in the present invention.

If any 2 of these 3 criteria indicate a normal ECG signal, i.e. only one or no "abnormal" signal is generated (stage 11) an output signal indicating absence of fibrillation is emitted (stage 12). However if at least 2 of these criteria indicate an abnormal ECG signal a rate detection routine 13 is initiated to confirm the presence of fibrillation.

The rate detection routine is shown in flow chart 13. After setting up the initial registers required the samples from the automatic gain control 4 are stored and 250 successive samples are differentiated and the steepest negative slope from the gradients obtained is determined (stage 13a) to give a reference value. Limits of ±20% of this reference value are then set (13b). The remainder of the samples are differentiated (13c) and in stage 13d the gradients are scanned for values within the limits determined at stage (13b). If no gradient within these limits is detected within 3 seconds (i.e. within 750 samples) stage 13d causes a "no rate detected" signal to be emitted. If a gradient within the limits a counter 13e is started to measure the time elapsing before the next slope within these limits is detected. If no such slope is detected within the 3 seconds following the first slope detected a "no rate detected" signal is again emitted (stage 13f): if the time elapsed is less than 3 seconds the time recorded is stored (13g). The counter is then set to zero (13h) and the procedure of stages 13e to 13h is repeated until a total of 8 times between gradients has been accummulated.

The mean of these times is then calculated (13i) and limits of ±20% of this mean are set (13j). The number of individual times within these limits is then deduced (13k) and if at least 5 out of the 8 times are within the limits an "ECG normal" signal is emitted by stage 12. If 4 or less of the times are outside these limits a "ventricular fibrillation detected" signal is emitted.

The rate detection routine thus indicates fibrillation when either the maximum negative gradient is not repeated for 3 seconds or when at least half of the intervals between these gradients differ from the mean by more than 20%.

In order to avoid a false result because of artifact the procedure of stages 13a and 13b may be repeated on successive batches of 250 samples and the lesser of the reference gradients obtained taken as a standard.

The arrangement described above is capable of analyzing an ECG signal and indicating possible fibrillation within 15 seconds and may be used in a hospital ward, especially an intensive care unit, to indicate malfunction of a patient's heart rapidly. Instead of or in addition to a visual or acoustic output the apparatus could be connected to a defibrillator to administer a defibrillation shock to the patient when fibrillation is indicated.

The above-described procedure for detecting ventricular fibrillation may be operated using a computer of known type which contains a programme to carry out the necessary logic operations. The computer may be connected to a graphic terminal to display the fluctuating signal from the patient visually when a signal indicating fibrillation is emitted by the computer, and to a hand copy unit to print out a permanent record of the signal from the patient if required. The computer may comprise one or more microprocessors, suitably programmed, and microprocessors which may be used include those available commercially under the following designations. Motorola 6800, Intel 8080, 8085, 8086 and 8048, Zilog Z80 and Z8000, Mostck/Fairchild 3870, Texas Instruments 9900 series and RCA 1802. The use of a microprocessor may enable a fully portable unit capable of detecting fibrillation and administering a defibrillation shock to be provided, for use in emergency situations in the field as well as in hospitals.

We claim:

1. Pattern recognition apparatus comprising a pair of electrodes for connection to the body of a patient to receive an electric signal fluctuating about an isoelectric line, a filter for attenuating signals having a frequency below 3 Hz and above 18 Hz having an input connected to the electrodes and an output, sampling and converting means having an input connected to the output of the filter for taking samples of the filtered signals at intervals and converting the magnitudes of the samples from analogue to digital form, and an output, automatic gain control means having an input connected to the output of the sampling and converting means responsive to the digitised samples for standardising the magnitudes of the digitised samples to a predetermined maximum value, and an output and analyzing means having an input connected to the output of the automatic gain control means for receiving the standardised samples and for analyzing the standardised samples to detect an abnormal physiological condition, said analyzing means comprising totalling means for totalling the magnitudes of the samples respectively above and below the isoelectric line for successive batches of samples, for calculating the ratios of the totals so obtained, for calculating the mean of the ratios, for calculating the proportion of the ratios which are within predetermined limits above and below the mean and for generating a first signal if this proportion is below a predetermined value, zero proportion means for calculating the proportion of samples of zero magnitude from a batch of successive samples and for generating a second signal if this proportion is below a predetermined value, differentiation means for differentiating groups of samples in a batch with respect to time to determine the gradients of each group, for calculating the variance of the gradients in the batch and for generating a third signal if the variance exceeds a predetermined value, means responsive to said first, second and third signals for generating a fourth signal if any two of said first, second and third signals are generated, and means responsive to said fourth signal for differentiating a group of successive samples in a batch with respect to time, for calculating the greatest negative slope obtained as a reference value, for differentiating subsequent groups of the batch, for calculating the time intervals between successive negative slopes which are between predetermined slope limits above and below said reference value, for calculating the mean of said time intervals, for calculating the proportion of intervals within predetermined time limits above and below said mean and for generating a fifth signal indicating an abnormal condition if said proportion is below a predetermined value, 2. Apparatus according to claim 1, wherein said totalling means comprises means for setting limits respectively above and below the isoelectric line and for totalling only the samples above and below the respective upper and lower limits.

3. Apparatus according to claim 1 wherein said totalling means comprises means for calculating the proportion of said ratios of the totals within 20% of the mean value of said ratios of the totals.

4. Apparatus according to claim 3 in which said totalling means comprises means for generating said first signal if said proportion is less than 4 out of 6.

5. Apparatus according to claim 1 wherein said totalling means for totalling the magnitudes of the samples respectively above and below the isoelectric line for successive batches of samples, each batch containing the samples from a duration of 2 seconds.

6. Apparatus according to claim 1, in which said zero proportion means comprises means for setting a limit above the isoelectric line and counting all the sample magnitudes below said limit as zero.

7. Apparatus according to claim 6, in which said zero proportion means comprises means for inverting the samples, again calculating the proportion of samples of zero magnitude and generating said second signal if said proportion of samples of zero magnitude is less than a predetermined value for both the inverted and the uninverted samples.

8. Apparatus according to claim 6 or 7, in which said zero proportion means comprises means for setting a limit above the isoelectric line of 20% of the maximum magnitude of the standardised digital samples and generating said second signal if less than 68% of the magnitudes are counted as zero.

9. Apparatus according to claim 1, in which said means responsive to the fourth signal comprises means for calculating the time intervals between successive negative slopes which are between 20% above and 20% below the greatest negative slope.

10. Apparatus according to claim 1 in which said means responsive to the fourth signal comprises means for calculating the proportion of intervals which are between 20% above and 20% below said mean of said time intervals.

11. Apparatus according to claim 1, in which said means responsive to the fourth signal comprises means for calculating 8 successive said time intervals and for generating said fifth signal if no more than 4 intervals are within said predetermined time limits.

12. Apparatus according to claim 1 in which said means responsive to the fourth signal comprises means for generating said fifth signal if one of said time intervals exceeds 3 seconds.

13. Apparatus according to claim 1, in which said means responsive to the fourth signal comprises means for differentiating two groups of successive samples from a batch of samples and calculating the lower of the greatest negative slope from each of said two groups as said reference value.

14. Apparatus according to claim 1, comprising a warning device responsive to said fifth signal.

15. Apparatus according to claim 1 comprising a defibrillator responsive to said fifth signal for administering a defibrillating shock to the body of said patient.

* * * * *